United States Patent
Hecker et al.

(10) Patent No.: US 7,320,964 B2
(45) Date of Patent: Jan. 22, 2008

(54) MODULATION OF EXPRESSION OF STAT-1 DEPENDENT GENES

(75) Inventors: Markus Hecker, Göttingen (DE); Andreas H. Wagner, Göttingen (DE)

(73) Assignee: Avontec GmbH, Martinsried (DE)

( * ) Notice: Subject to any disclaimer, the term of this patent is extended or adjusted under 35 U.S.C. 154(b) by 276 days.

(21) Appl. No.: 10/491,644

(22) PCT Filed: Oct. 2, 2002

(86) PCT No.: PCT/DE02/03747

§ 371 (c)(1),
(2), (4) Date: Dec. 9, 2004

(87) PCT Pub. No.: WO03/031459

PCT Pub. Date: Apr. 17, 2003

(65) Prior Publication Data

US 2005/0192238 A1    Sep. 1, 2005

(30) Foreign Application Priority Data

Oct. 4, 2001  (DE) ................. 101 48 828

(51) Int. Cl.
*A61K 31/70* (2006.01)
*C07H 21/04* (2006.01)
*C12N 5/00* (2006.01)
*C12Q 1/68* (2006.01)

(52) U.S. Cl. ............... 514/44; 435/6; 435/23.1; 435/24.1; 435/24.5

(58) Field of Classification Search ............ None
See application file for complete search history.

(56) References Cited

U.S. PATENT DOCUMENTS

2004/0048820 A1*  3/2004  Hecker et al. ............ 514/44

FOREIGN PATENT DOCUMENTS

| WO | WO 95/08001 | 3/1995 |
|---|---|---|
| WO | WO 95/11687 | 5/1995 |
| WO | WO 02/29044 | 4/2002 |

OTHER PUBLICATIONS

Huang et al., "Role of Janus kinase (JAK)/signal transducters and activators of transcription (STAT) cascade in advanced glycation end-product-induced cellular mitogenesis in NRK-49F cells," *Biochem. J.*, 342:231-238, 1999.
Krzesz et al., "Cytokine-inducible CD40 gene expression in vascular smooth muscle cells is mediated by nuclear factor κB and signal transducer and activato of transcription-1," *FEBS Lett.*, 453:191-196, 1999.
Lauth et al., "Transcriptional control of deformation-induced preproendothelin-1 gene expression in endothelial cells ," *J. Mol. Med.*, 78(8):441-450, 2000.
Lee and Beneveniste, "Stat1 α expression is involved in IFN-γ induction of the class II transactivator and class II MHC genes," *J. Immunol.*, 157:1559-1568, 1996.
Mann and Dzau, "Therapeutic applications of transcription factor decoy oligonucleotides," *J. Clin. Invest.*, 106(9):1071-1075, 2000.
Morishita et al., "A gene therapy strategy using a transcription factor decoy of the E2F binding site inhibits smooth muscle proliferation in vivo," *Proc. Natl. Acad. Sci., USA*, 92(13):5855-5859, 1995.
Morishita et al., "Gene therapy in vascular medicine: recent advances and future perspectives," *Pharmacology and Therapeutics*, 91:105-114, 2001.
Ohmori et al., "Synergy between interferon-gamma and tumor necrosis factor-alpha in transcriptional activation is mediated by cooperation between signal transducer and activator of transcription 1 and nuclear factor kappaB ," *J. Biol. Chem.*, 272(23):14899-14907, 1997.
Schieffer et al., "Role of NAD(P)H oxidase in angiotensin II-induced JAK/STAT signaling and cytokine induction ," *Circ. Res.*, 87(12):1195-1201, 2000.
Stephanou et al., "Ishemia-induced STAT-1 expression and activation play a critical role in cardiomyocyte apoptosis," *J. Biol. Chem.*, 275(14):10002-10008, 2000.
Varga et al., "Antisense strategies: functions and applications in immunology," *Immunology Letters*, 69:217-224, 1999.

* cited by examiner

*Primary Examiner*—Sean McGarry
(74) *Attorney, Agent, or Firm*—Fulbright & Jaworski L.L.P.

(57) ABSTRACT

The invention relates to decoy oligonucleotides and antisense oligonucleotides comprising a nucleic acid sequence according to SEQ ID NO: 1 to 43, in addition to the use of said nucleotides as medicaments.

4 Claims, 8 Drawing Sheets

MODULATION OF EXPRESSION OF STAT-1 DEPENDENT GENES

Figure 1:
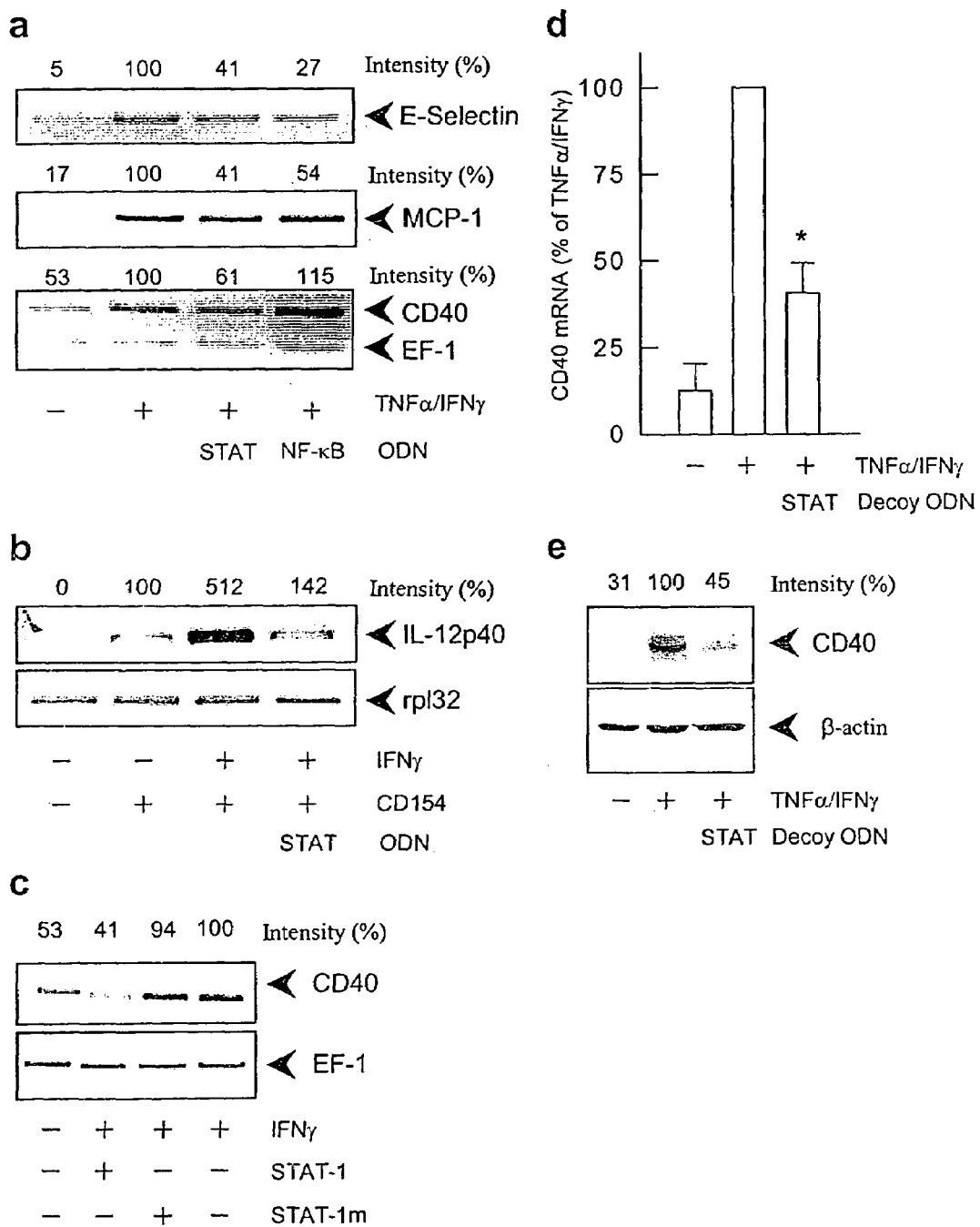

This application claims priority to PCT/DE 02/03747, filed on Oct. 2, 2002. The entire content of this application is incorporated herein by reference.

The present invention relates to decoy-oligonucleotides and antisense-oligonucleotides having the nucleic acid sequence according to SEQ ID NO: 1 to 43 as well as the use thereof as medicaments.

It is a major aim of the decipherment of the human genome to identify morbid genes (due to the mode of action of their products) and morbid changes in the structure of these genes (polymorphisms) respectively and to assign them to a disease pattern. Therefore a causally determined therapy for most diseases has come into reach if it is accepted that these are caused by a defined number of gene products being expressed too strongly, too weakly or deficiently. In fact the usually singular genetic defect (monogenetic diseases) is already known for a set of hereditary diseases (e.g. cystic fibrosis) whereas the situation for other diseases (e.g. hypertension) turns out to be considerably more complex. The latter are obviously not the result of a single but multiple genetic defects (polygenetic disease) predetermining the affected persons to develop the disease in coincidence of certain environmental factors. Albeit this constraint the targeted intervention in the expression of one or multiple genes affords the opportunity of a cause- and not only a symptom-based therapy.

Transcription factors are DNA-binding proteins that attach to the promoter region of one or multiple genes inside the cell nucleus thereby regulating their expression, i.e. the regeneration of the proteins these genes are coding for. Besides the physiologically important role of controlling developmental and differentiation processes in the human body, transcription factors display a high potential for eliciting a disease particularly if they activate the gene expression at a wrong point of time. In addition (possibly the same) transcription factors can block genes with a protective function und act predisposing for the formation of a disease. Insofar the in the following described principle of an anti-transcription factor therapy aims at the inhibition of morbid genes and the activation of protective genes in contrast.

Inflammation is a defense reaction of the organism and its tissues against damaging stimuli aiming at the remediation of the damage or at least its local limitation and at abolishing the cause of damage (e.g. invaded bacteria or foreign substances). The elicitors of an inflammation can be microorganisms (bacteria, viruses, fungi or parasites), foreign substances (pollen, crystals of asbestos or silicates), destruction of the tissue by mechanical impairment, chemical noxa and physical influences as well as elicitors from the body itself (collapsing tumour cells, extravasal blood, autoimmune reactions) or crystals of intra-bodily precipitated substances (uric acid, calcium oxalate and calcium phosphate, cholesterol).

The rapid activation of mastocytes (inside the tissue) or of basophile granulocytes in the blood is an example for the tripping of a very strong acute-inflammatory response and is discriminatory for immunological hypersensitivity reactions of the immediate type (humoral allergy type I). If the organism got into contact with an antigen (or an allergen, respectively, in the case of hypersensitivity) already beforehand B-lymphocytes had been sensitised as a reaction to this. The B-lymphocytes transform into plasmocytes in cooperation with previously sensitised CD4-positive type 2 T-helper cells (Th2 cells) and start producing antibodies of the IgE-type against the antigen. During this differentiation process the co-stimulation of the B-lymphocytes via the CD40-receptor by the Th2-cells expressing the respective ligand (CD154) is of crucial importance. When the antigen-loaded IgE-antibodies bind to the respective receptors (type $Fc_e$) on the mastocytes these start to release different mediators of inflammation especially histamine, interleukin-8, leukotrienes and tumour necrosis factor-α (TNFα). Consequence of which is the attraction of professional inflammatory cells especially of eosinophile and neutrophile granulocytes and monocytes but also of T-lymphocytes on-the-spot (chemotaxis). At the same time a histamine dependent vasodilatation and increase of permeability of the endothelial cells coating the interior vascular wall takes place. Due to the vascular dilatation the flow velocity decreases facilitating the establishment of the physical contact between the attracted leukocytes and the endothelial cells. These endothelial cells being exposed to cytokines (e.g. TNFα) and thereby already activated display an intensified expression of selectins on their luminal surface (e.g. E-selectin) causing a rolling along the endothelial cells of the leukocytes and thereby the activation of further adhesion molecules (integrins; e.g. intercellular adhesion molecule-1 [ICAM-1] or vascular cell adhesion molecule-1 [VCAM-1]). The leukocytes can now adhere to the vascular wall (margination) and the histamine-related increase in permeability (loosening of the union of endothelial cells) favours their migration into the extravasal space (diapedese). At the same time augmented amounts of protein rich fluid (inflammatory exudate) attain the interstitial space forming an oedema. Circumjacent nerve endings are irritated by the increasing pressure in the tissue and by further mediators generated by the inflammatory cells and trigger pains making the damage of the tissue aware.

The granulocytes which have migrated to the site of inflammation and the monocytes which have re-differentiated into macrophages attempt to eliminate the causers of the inflammation by phagocytosis and lysis respectively thereby triggering the release of inter alia proteolytic enzymes and oxygen radicals that may damage also the surrounding tissue. In particular the activation of the macrophages can account in many ways for the fact (e.g. by the release of further cytokines like interleukin-1β or interleukin-6) that the entire organism is involved by the primarily local inflammatory response in terms of an acute phase response. Representative characteristics of an acute phase response are fatigue, lassitude and fever, an increased release of leukocytes from the bone marrow (leukocytosis), the detection of acute phase proteins in the blood (e.g. C-reactive protein), the stimulation of the immune system as well as weight loss due to a changed status of the metabolism.

If the cause of the inflammation can be eliminated the process of wound healing falls into line with the destroyed tissue being repaired. At best this amounts to an entire re-establishment (restitutio ad integrum), whereas bigger lesions or an excessive production of connective tissue (especially collagen) result in the formation of a scar which is possibly associated with considerable dysfunctions depending on the affected tissue. If the cause cannot be eliminated at once (foreign substances or wound infection) the wound healing is delayed at simultaneous increase of the immigration and activity of the phagocytes bringing about the doom of the tissue (necrosis) up to the formation of cavities (abscess). The result is almost always a scarred re-structuring of the tissue with a respective loss of function.

If the local limitation of the inflammation which is derived from the causative agent does not succeed, the inflammation spreads over the entire organism via the lymphatic system. The consequence is a sepsis with a possibly fatal upshot (septic shock).

Wound healing is also interfered with if the inflammatory and the healing process are in balance. The result is a chronic inflammation which may be fibrosing (excessive synthesis of collagen) or granulomatous (organisation of inflammatory cells into a granulation tissue) and usually brings about a continuous destruction and increasing constraint of functionality of the affected tissue respectively.

Besides the depicted common inflammatory response which may degenerate chronically there are inflammatory diseases that exhibit both common grounds and distinct differences with regard to the underlying pathogenesis. Two inflammatory diseases of such kind are for example complications after cardio-surgical interventions and the immunological incompatibility reactions which more space in this specification is dedicated to because of their enormous clinical relevance.

The balloon-tipped catheter based mechanical dilatation (percutaneous angioplasty) and the bypassing of arteriosclerotically stenosed arteries by means of venous bypasses respectively still constitute the therapies of choice in patients with coronary and peripheral circulatory disorders respectively in order to provide protection against an imminent infarction or organ failure. But the rate of re-occlusion (restenosis) of the arteries which were mechanically dilated and (in the majority of cases) treated with a metallic vascular support (stent) appears unacceptably high with 20-50% within 6 months. Also the rate of re-occlusion of aortocoronary and peripheral venous bypasses respectively with 50-70% after 5 years is more than dissatisfactory for the treated patients in particular against the background of the risk around the procedure and the postoperative risk respectively. Presumably because of the damage of the vascular wall (hereby both the endothelial and the smooth muscle cells being affected) the restenosis after angioplasty shows particularly in the early stage a pronounced inflammatory component being characterised inter alia by the infiltration of the vascular wall with professional inflammatory cells (above all monocytes and T-lymphocytes). The fibro-proliferating stenosis formation (intimal hyperplasia) in aortocoronary and peripheral venous bypasses respectively seems to be based also on a inflammatory reaction which in particular is caused by mechanical and physical noxa. It has been known for a long time also that the so called ischemia/refusion-related damage in the context of surgical interventions or organ transplantations is accompanied by an inflammatory-based tissue damage in which the interaction between endothelial cells and professional inflammatory cells (above all granulocytes but also monocytes and T-cells) as well as the release of tissue damaging substances (oxygen radicals, cytokines) play a quite crucial role.

In connection with the mentioned cardio-vascular complications it is important that there are protective mechanisms, above all in the endothelial and smooth muscle cells of the vascular wall, which help to limit the extent of the inflammatory response and the subsequent adaptive re-structuring of the tissue. To this for example belongs the synthesis of nitric oxide (NO) by the NO-synthase in the endothelial cells. NO, probably featuring the endogenous antagonist of the oxygen radical superoxide, inhibits inter alia the expression of pro-inflammatory chemokines (e.g. monocyte chemoattractant protein-1, MCP-1) and of adhesion molecules (e.g. ICAM-1) in endothelial cells, the expression of receptors for growth factors in smooth muscle cells (e.g. endothelin B-receptor) as well as the release of growth factors from leukocytes. Insofar it is easy to comprehend that a mechanical damage just as a functional damage of the endothelium (e.g. by a cytokine-induced reduction of the expression of the NO-synthase in these cells) counteract the processes of inflammation and subsequent fibro-proliferating re-structuring of the vascular wall which form the basis for the mentioned cardio-vascular complications.

All previous attempts to check the restenosis after angioplasty medicamentously have not achieved the desired effect in the majority of patients. At present two local principles of therapy are favoured: the already approved vascular brachy-therapy, a method for checking the cell growth by short-time radioactive irradiation of the dilated vascular section and the drug-eluting stents which are still in the clinical trial. This method comprises polymer coated stents which are "impregnated" by growth inhibiting medicaments (cytostatic and immunosuppressive agents) and release them slowly during a period of several weeks. Most recent clinical studies prove that both therapeutic approaches are not exempt from to some extent serious problems (e.g. in-stent-thrombosis running the danger of an infarction) despite of encouraging results at the beginning.

Besides the already delineated immunological type I-incompatibility reaction there are in principle four other forms of allergy and dysfunctions in the immune regulation respectively. The type I-reaction itself can in principal be sorted into two phases after allergisation was accomplished: the rapid release and regeneration of vascularly active inflammatory mediators from IgE-spiked mastocytes and the late reaction which is mediated by the attracted eosinophile and neutrophile granulocytes. The complete type I-reaction can take place either locally or systemically in dependence on the exposure to the allergen. Allergens in the respiratory air elicit reactions in the respiratory tract, typically accompanied by mucosal oedemas and hypersecretion (allergic rhinopathy, hay fever) as well as bronchospasm (asthma) whereas allergens in the nourishment elicit gastrointestinal symptoms like nausea, vomitus and diarrhoea. The skin reacts on allergens with itching and urticaria as well as atopic dermatitis (neurodermatitis) But if the allergen gains direct access to the bloodstream (e.g. infusion of blood products, medicaments) or if the exposure to the allergen is especially strong, a systemic immediate reaction results possibly entailing a life-threatening decrease of the blood pressure (anaphylactic shock).

In the case of the type II-reaction antigenically active cells (e.g. extraneous blood cells) or extracellular proteins (e.g. medicament-induced changes at the surface of a cell naturally produced in the body) take centre stage. After allergisation the second contact leads to the production of allergen-specific antibodies of the IgG- and IgM-type which bind to the allergenic cell in great quantities (opsonisation). Hereby the complement system (formation of a membrane attacking complex) and a special subpopulation of lymphocytes, the natural killer cells (NK-cells), are activated. The result is a destruction of the allergenic cell by cytolysis. A similar reaction is elicited when auto-antibodies attach to structures that are naturally produced in the body such as the basal membrane of the glomerular capillaries and thereby eliciting a rapidly progressive glomerulonephritis with imminent renal insufficiency. Besides the type 1 T-helper cells (Th1-cells, see below) the activated NK-cells are the main producers of interferon-γ, a cytokine that massively intensifies the inflammatory response in particular by the activation of macrophages.

The type III-reaction is characterised by the formation and deposition of immune-complexes (antigen-antibody-complexes) with subsequent activation of the complement system and phagocytes (granulocytes, macrophages). They circulate in the blood and successively deposit mainly in the capillaries of the renal glomeruli but also in the joints or in the skin. The hereby elicited inflammatory response may bring about a (immune-complex-) glomerulonephritis, pains in the joints as well as urticaria. Infections can also elicit a systemic type III-reaction if the immune system fails to eliminate the causative agent (e.g. streptococci). Representative local type III-reactions are the so called Arthus-reaction in the skin after an immunisation or the exogenous allergic alveolitis in the case of the deposition of antigen-antibody-complexes in the lung (e.g. bird-breeder's lung). The systemic lupus erythematodes is a type III-reaction as well but in terms of an autoimmune disease due to the formation of auto-antibodies.

In contrast to the hypersensitivity reactions mentioned before the type IV-reaction is not humoral but cell constrained and reaches its maximum usually not until after several days (delayed type of reaction or delayed type hypersensitivity). Elicitors are mainly proteins, invaded foreign organisms (bacteria, viruses, fungi and parasites), other foreign proteins (e.g. wheat-derived gliadin in the case of celiac disease) as well as haptens (medicaments, metals [e.g. nickel in the case of contact dermatitis], cosmetics and plant components). The primary rejection of transplanted organs is also a type IV-reaction. The antigen is phygocytised by (tissue) macrophages, processed and presented to naive T-helper cells (CD4-positive); the allergisation of the T-helper cells takes several days. At the second contact the in such a way sensitised T-helper cells alter in Th1-cells; thereby the CD154-mediated co-stimulation of the antigen-presenting cell (this one expresses the CD40-receptor) plays an important role because this signalling pathway triggers the release of interleukin-12 from the macrophages. Interleukin-12 initiates the differentiation and proliferation of the T-helper cells. The Th1-cells on their part excite the formation of monocytes in the bone marrow by certain growth factors (e.g. GM-CSF), recruit these by means of certain chemokines (e.g. MIF) and activate them by the release of IFNγ. The hence resulting very strong inflammatory response may destroy tissue normally produced in the body (e.g. tuberculosis) or transplanted tissue in a large scale. Moreover CD8-positive cytotoxic T-cells are involved in the transplant rejection (cytolysis) with the CD8-positive cytotoxic T-cells being able to recognise their target (the foreign cell surface) and to "arm" themselves accordingly only by a preceding antigen-presentation like the CD4-positive Th1-cells.

A dysfunction of the immune regulation similar to a type IV-reaction forms the basis for e.g. the rheumatoid arthritis or the multiple sclerosis (auto-reactive Th1-cells) as well as for diabetes mellitus (auto-reactive cytotoxic T-cells). T-cells being directed against certain antigens of the causative agent (e.g. streptococci) which cross-react with auto-antigens (produced in the body; molecular mimicry) might potentially play a role at these autoimmune diseases besides bacterial super-antigens (e.g. the causative agent of TBC) and the according genetic predisposition (MHC-proteins, Th1/Th2-imbalance). In contrast, type V-reactions may be evoked inter alia by activating or blocking auto-antibodies of hormone- (e.g. thyrotropin in the case of Basedow's disease) or neurotransmitter-receptors (e.g. acetylcholine in the case of myasthenia gravis).

Comparable with the transplant rejection—yet in the reverse sense—is the graft versus host disease (GVHD) which appears in the course of allogenic bone marrow transplantations (between genetically non identical individuals) in about 40% of the recipients. During the acute-phase lasting up to three months the T-cells of the donor which have been transfused with the stem cells attack the host organism. The resulting possibly severe inflammation response becomes manifest preferably in the skin, the gastrointestinal tract and in the liver.

For the treatment of acute inflammatory diseases in dependence on to the assumed cause usually non-steroidal antiphlogistics (NSAIDs, inter alia inhibition of the synthesis of prostaglandins) and/or anti-infectious agents (devitalisation of bacteria, fungi or parasites) and antiviral chemotherapeutics respectively, contingently also glucocorticoids (general inhibitors of gene expression) in a local application, are utilised. In the case of severe or chronically recurring inflammatory diseases glucocorticoids or immunosuppressive agents (inhibition of the T-cell-activation) or cytostatics such as methotrexate are systemically administered. This also applies to the transplantation of organs and bone marrow respectively. Despite of their undisputable therapeutic effect a systemic administration of the mentioned pharmaceuticals can evoke severe side effects especially when permanently used. So for example up to 25% of the patients who take methotrexate for 2 or more years develop a severe cirrhosis of the liver. More recent active agents that are used in particular with chronically recurring inflammatory diseases block the pro-inflammatory effect of TNFα: antibodies directed against the cytokine itself and its receptor respectively, low-molecular antagonists of the receptor as well as a recombinantly produced, soluble receptor protein that traps the cytokine. But there is a growing number of indications for an increased incidence of infectious diseases during the therapy with the receptor protein (inter alia tuberculosis), and about 40% of the patients do not seem to respond to the therapy at all (non-responder). Also for the approved humanised TNFα-antibody there are according warning notices concerning the incidence of infections ranging up to sepsis 2-4 years after the start of the therapy. Moreover both active agents are contraindicated during an acute incident. In addition low-molecular antagonists of the receptor are approved for leukotrienes which are mainly used in the therapy of asthma as well as inhibitors of the cyclooxigenase-2, a new group of non-steroidal antiphlogistics (NSAIDs) with considerably reduced gastrointestinal side effects in comparison to the classical NSAIDs. Moreover there is a series of further—usually humanised—antibodies or antisense-oligonucleotide based approaches against adhesion molecules of leukocytes and endothelial cells respectively, cytokine receptors of T-helper cells or IgE-antibodies which are residing in different phases of the clinical trial. To refrain from the glucocorticoids and the anti-infectious agents as a group, the mentioned pharmaceuticals have in common to be directed specifically against a target molecule which is of relevance for the therapy.

The present invention is therefore based on the problem to provide substances for the prevention or therapy of excessive inflammatory responses and for the herewith associated implications for morbidity and mortality of the affected patients.

The problem is solved by the subject-matter defined by the patent claims.

The invention is elucidated by the following figures in greater detail:

FIG. 1 shows the inhibition of the cytokine-stimulated expression of CD40 (a, c, d and e), E-selectin and MCP-1(a) and of the CD40-ligand-induction of the interleukin-12p40-expression (b) in cultivated human endothelial cells by neutralisation of the transcription factor STAT-1 by means of an according cis-element-decoy (SEQ ID NO: 33). (a) Representative RT-PCR-analysis of the E-selectin, MCP-1 and CD40 mRNA-expression (in addition the densitometric analysis ("intensity") specified in % of the stimulated control and referring to the internal standard EF-1) in endothelial cells which had been pre-incubated with a STAT-1 (SEQ ID NO: 33) or NF-κB cis-element decoy (10 μM) for 4 hours and subsequently incubated with 100 U/ml tumour necrosis factor-α and 1000 U/ml interferon-γ for 9 hours. (b) Representative RT-PCR-analysis of the mRNA-expression of interleukin-12p40 (in addition the densitometric analysis ("intensity") specified in % of the stimulated control and referring to the internal standard rp132) in endothelial cells which had been pre-incubated with a STAT-1 cis-element decoy (10 μM; SEQ ID NO: 33) for 4 hours and subsequently incubated with about 670000 P3xTB.A7-cells/ml (these mouse myeloma cells stably express the human CD40-ligand CD154) and 1000 U/ml interferon-γ for 12 hours. (c) Representative RT-PCR-analysis of the CD40 mRNA-expression (in addition the densitometric analysis ("intensity") specified in % of the stimulated control and referring to the internal standard EF-1) in endothelial cells which had been pre-incubated with a STAT-1 cis-element decoy (SEQ ID NO: 33) or the respective control oligonucleotide (STAT-1-25mut) for 4 hours (concentration 10 μM) and subsequently incubated with 100 U/ml tumour necrosis factor-a and 1000 U/ml interferon-γ for 9 hours. (d) Statistical summary of 5 independent experiments on the effect of the STAT-1 cis element decoys (SEQ ID NO: 33) on the cytokine-stimulated CD40 mRNA-expression the cultivated endothelial cells ($*p<0.05$ versus the stimulated control cells). (e) Representative western-blot-analysis in addition to the densitometric analysis ("intensity" specified in % of the stimulated control and referring to the internal standard β-actin) of the effect of the STAT-1 cis element decoys (SEQ ID NO: 33) on the cytokine-stimulated CD40 protein-expression the cultivated endothelial cells after 24 hours. Comparable results were obtained in further experiments.

Figure 2:
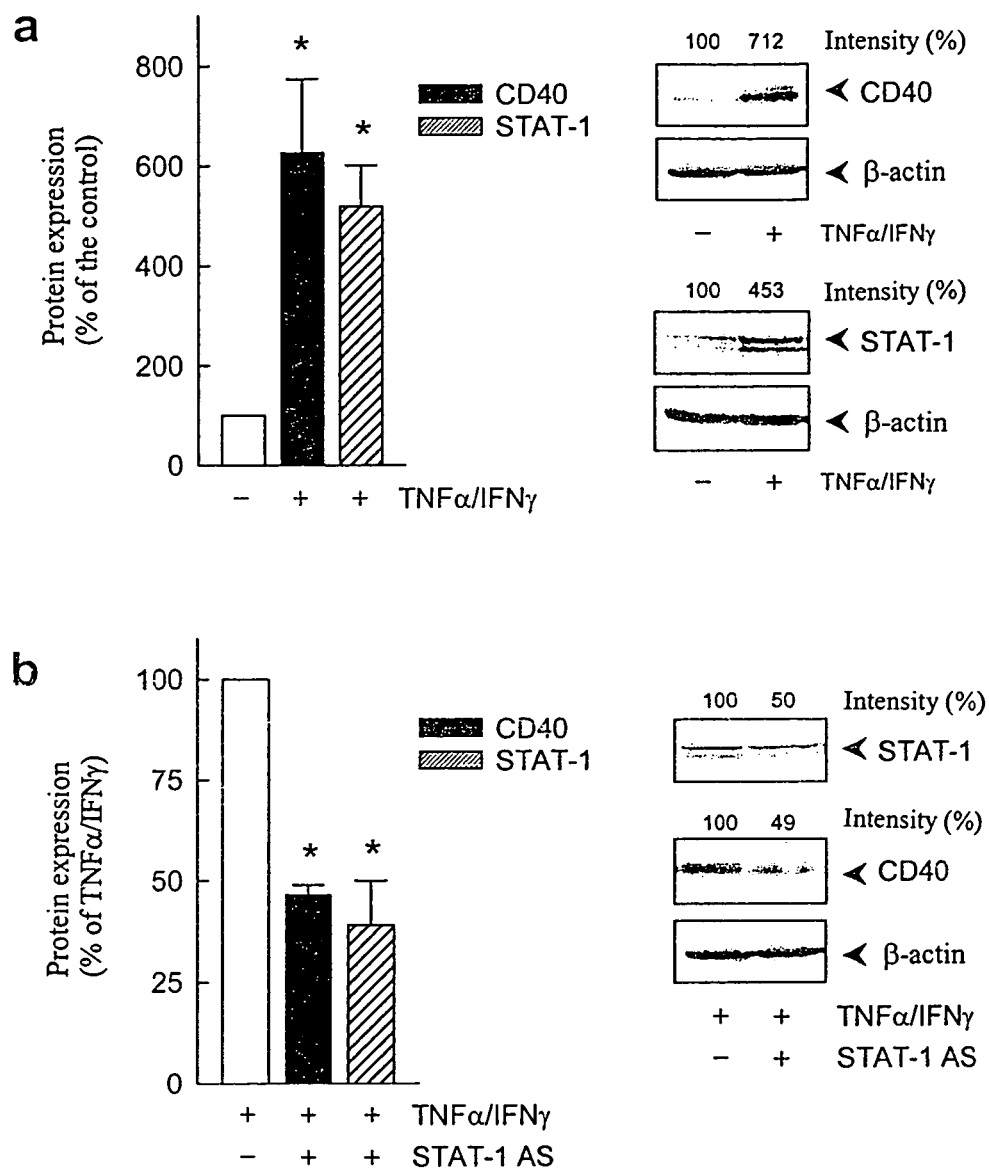

FIG. 2 shows the inhibition of the cytokine-induced expression of the CD40 gene in human cultivated endothelial cells by the antisense-oligonucleotide based down regulation of the expression of the transcription factor STAT-1. (a) Expression of the CD40- and STAT-1-protein respectively under resting conditions and after incubation of the cells with 100 U/ml tumour necrosis factor-α and 1000 U/ml interferon-γ for 14 hours. The left panel of the picture shows the statistical summary of 2-4 experiments with different batches of cells, the right panel of the picture shows each a representative western-blot-analysis in addition to the densitometric analysis ("intensity") specified in % of the non-stimulated control and referring to the internal standard β-actin ($*p<0.05$ versus the non-stimulated control cells). (b) Comparable inhibition of the CD40- and STAT-1-protein expression in stimulated endothelial cells by a pre-treatment with a STAT-1-antisense-oligonucleotide (1 μM; SEQ ID NO: 33) for 24 hours. Summary of 2 experiments (left panel of the picture; $*p<0.05$ versus the stimulated control cells) and representative western-blot-analysis (right panel of the picture).

Figure 3:
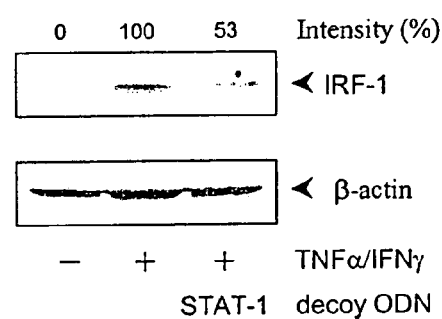
Figure 3:
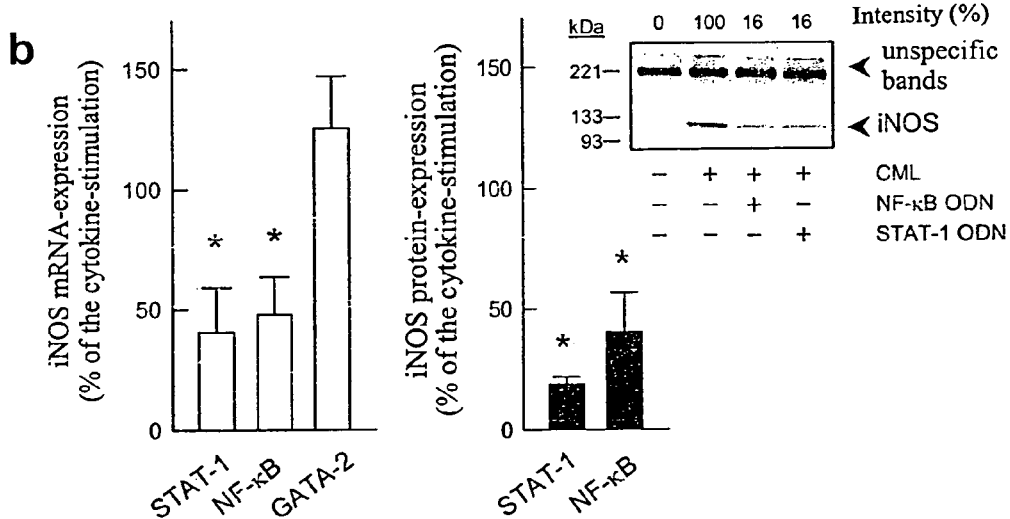

FIG. 3 shows the inhibition of the expression of the transcription factor IRF-1 in the monocyte-cell-line THP-1 (a) as well as of the inducible isoform of the NO-synthase in cultivated human smooth muscle-cells (b) by the neutralisation of the transcription factor STAT-1 by means of a respective cis-element decoy (SEQ ID NO: 33). (a) Representative western-blot-analysis in addition to the densitometric analysis ("intensity") specified in % of the stimulated control and referring to the internal standard β-actin. The cultivated THP-1-cells were pre-incubated with the cis-element decoy (10 μM) for 4 hours and subsequently incubated with 100 U/ml tumour necrosis factor-α and 1000 U/ml interferon-γ for 3 hours. (b) Left panel of the picture: statistical summary of 3 experiments with different batches of cultivated human smooth muscle cells which had been pre-incubated with a STAT-1 (SEQ ID NO: 33), a NF-κB or a GATA-2 cis-element decoy (10 μM) for 4 hours and subsequently incubated with 1000 U/ml interferon-γ, 60 U/ml interleukin-1β, 100 U/ml tumour necrosis factor-α and 1 μg/ml of a bacterial lipopolysaccharide for 9 hours. RT-PCR-analysis of the mRNA-expression for the inducible isoform of the NO-synthase ($*p<0.05$ versus the stimulated cells=100%). Right panel of the picture: statistical summary of 3 experiments with different batches of cells and representative western-blot-analysis of the inhibition of the cytokine-stimulated expression of the NO-synthase protein (after 20 hours of exposition) by pre-incubation with the STAT-1 (SEQ ID NO: 33) and NF-κB cis-element decoy respectively ($*p<0.05$ versus the stimulated cells=100%).

Figure 4:
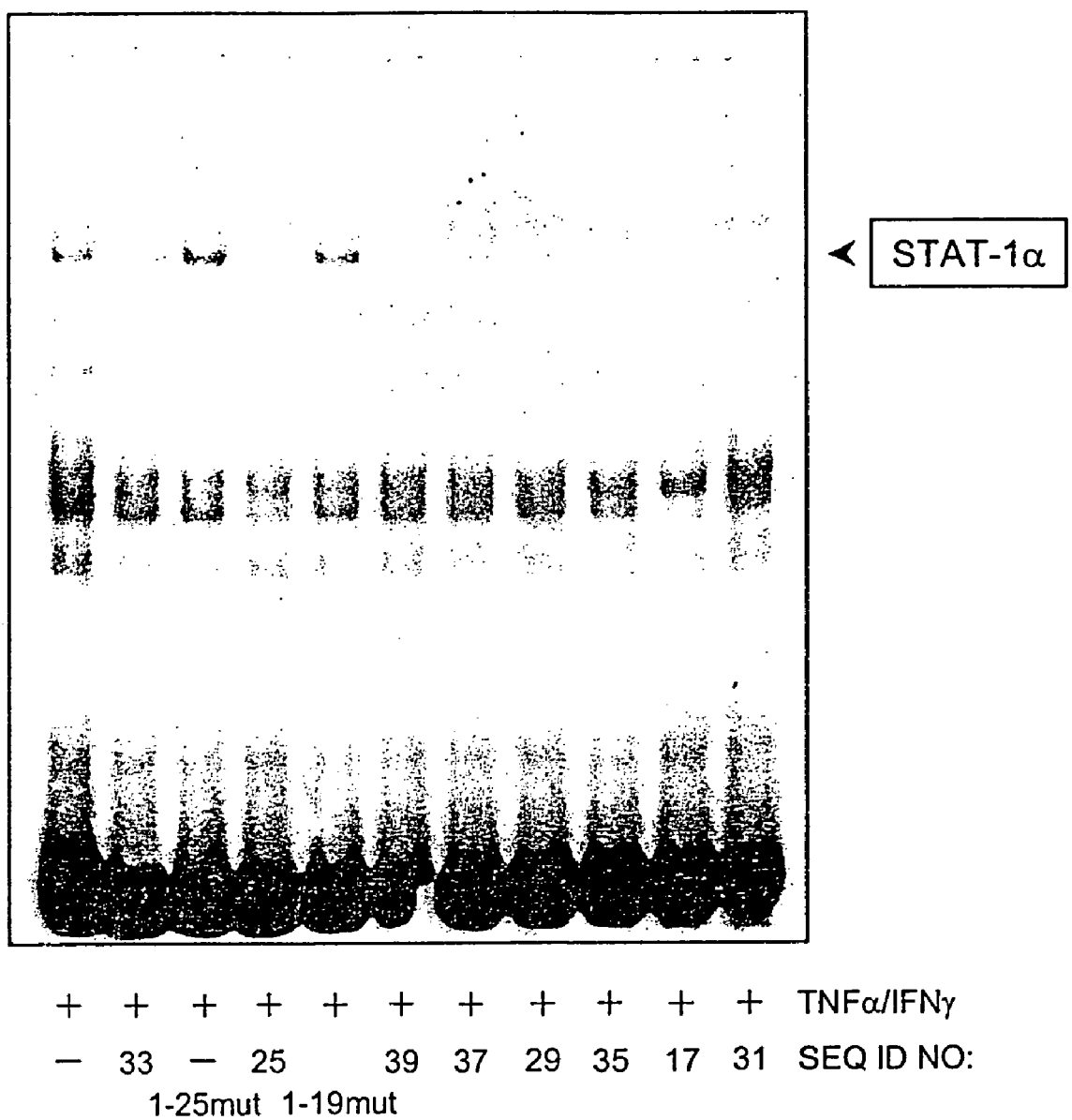

FIG. 4 shows the neutralisation of endogenous STAT-1 in extracts of cell nuclei of the monocyte-cell-line THP1 by different cis-element decoys (SEQ ID NO: 17, 25, 29, 31, 33, 35, 37, 39 and the mutated control-oligonucleotides STAT-1-19mut and STAT-1-25mut). Representative EMSA-analysis. Cultivated THP-1 cells were incubated with 100 U/ml tumour necrosis factor-α and 1000 U/ml interferon-γ for 3 hours and subsequently used for the preparation of nuclear extracts. The nuclear extract of the cells was co-incubated with the [$^{32}$P]-labelled double stranded SIE-oligonucleotide (Santa Cruz Biotechnologie, Heidelberg, Germany) and the respective cis-element-decoys and control-oligonucleotides respectively at room temperature for 20 minutes and was subsequently subjected to the electrophoretic mobility shift-analysis.

Figure 5:
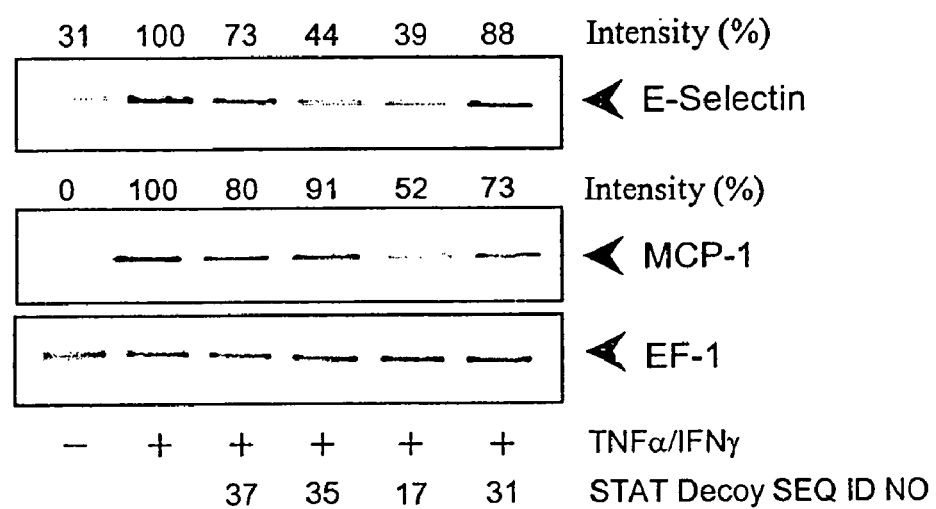

FIG. 5 shows the effect of selected STAT-1 cis-element decoys (SEQ ID NO: 17, 31, 35, 37) on the expression of E-selectin and MCP-1 mRNA in human smooth muscle cells from the thymus vein. The cultivated cells (passage 2) were pre-incubated with the respective cis-element decoys (10 μM) for 4 hours and subsequently incubated with 100 U/ml tumour necrosis factor-α and 1000 U/ml interferon-γ for 9 hours. Representative RT-PCR-analysis, comparable results were obtained in further experiments.

Figure 6:
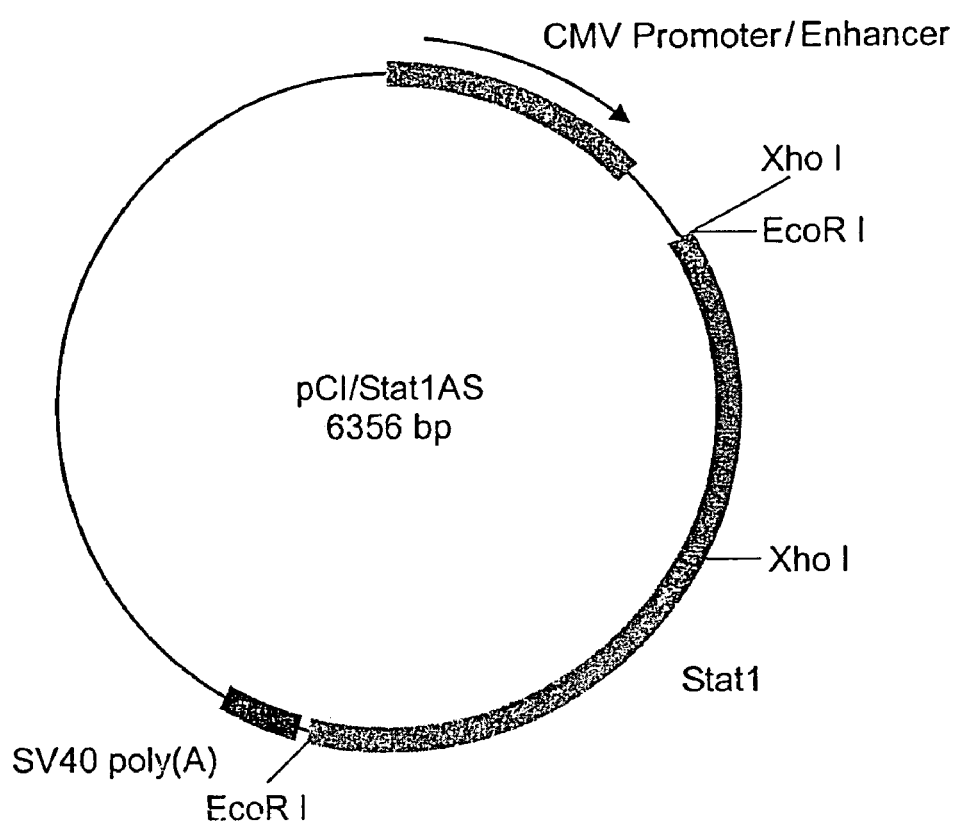

FIG. 6 schematically shows the structure of the STAT-1-antisense-expression vector pCI/Stat1 AS in terms of a gene map.

Figure 7:
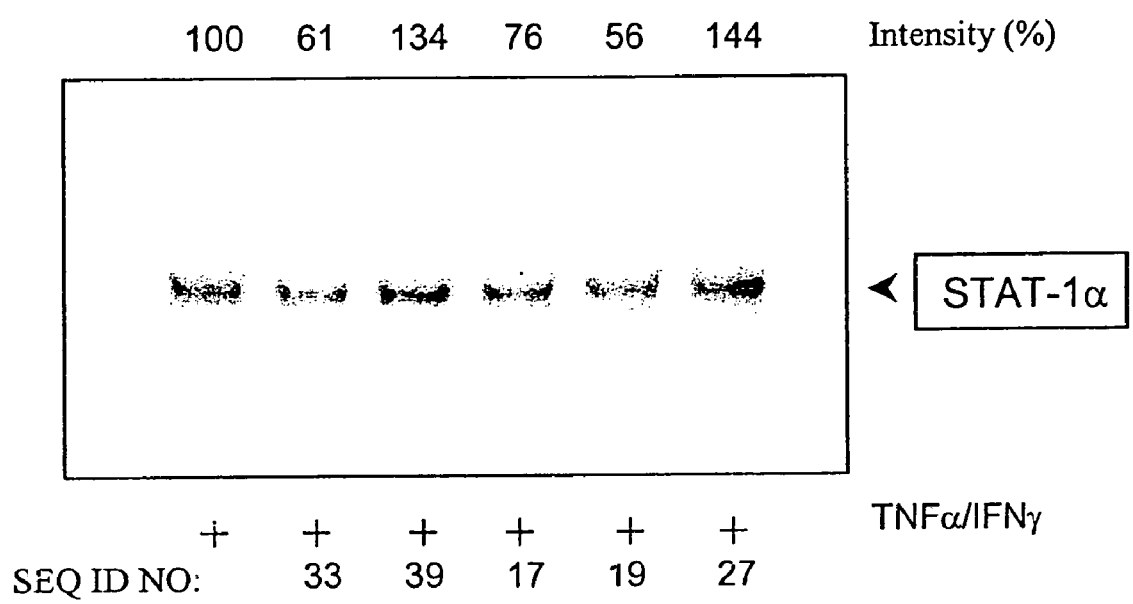

FIG. 7 shows the result of the neutralisation of STAT-1 in human cultivated endothelial cells by different cis-element decoys (SEQ ID NO: 17, 19, 27, 33 and 39). Representative EMSA-analysis in addition to the densitometric analysis ("intensity"). The cultivated endothelial cells were incubated with the decoy-oligonucleotides (10 μmol/l) for 4 hours and subsequently stimulated with 100 U/ml tumour necrosis factor-a and 1000 U/ml interferon-γ for 30 min. For the EMSA-analysis nuclear extracts of the stimulated cells and the [$^{32}$P]-labelled double stranded SIE-oligonucleotide (Santa Cruz Biotechnologie, Heidelberg, Germany) were used.

Figure 8:
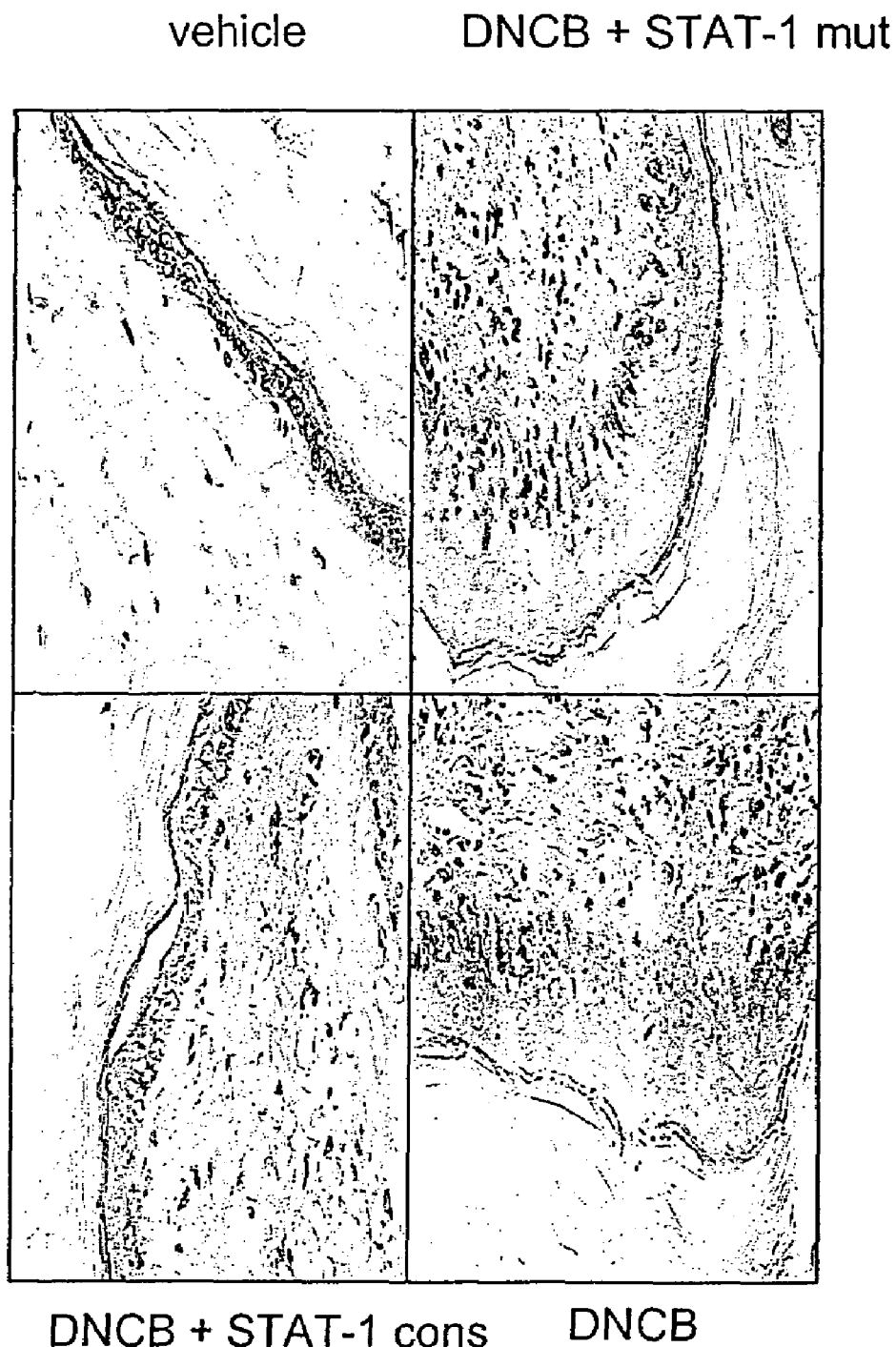

FIG. 8 shows the histological analysis of the effect of a STAT-1 decoy-oligonucleotide (STAT-1cons, 10 nmol, SEQ ID NO: 19) but not of a mutated control-oligonucleotide (STAT-1mut, 10 nmol, SEQ ID NO: 61) on the DNCB-induced contact-dermatitis in male guinea pigs (original× 400, typical result of 17 examined guinea pigs in total).

The inventors have characterised the transcription factors which take part in the cytokine-mediated increase of the expression of pro-inflammatory gene products (CD40, E-selectin, inducible isoform of the NO-synthase, interleukin-12 [p40], MCP-1) in human endothelial- and smooth muscle cells as well as in monocytes. Thereby it could be shown that there is a synergism between the transcription factors nuclear factor κB (NF-κB) and the signal transducer and activator of transcription-1 (STAT-1) in the case of the stimulation of the cultivated endothelial cells with TNFα and CD154 respectively in combination with IFNγ. The same holds true for the cultivated smooth muscle cells and monocytes respectively.

IFNγ alone was able to increase the expression of CD40 in human endothelial cells but not the one of E-selectin or interleukin-12. For the expression of those two gene products which are hardly and non-constitutively respectively expressed in endothelial cells a simultaneous stimulation of the cells with TNFα (E-selectin) and CD154 (interleukin-12) respectively is essential. Furthermore the de novo expression of an additional transcription factor, the interferon regulatory factor-1 (IRF-1), is necessary for the IFNγ-mediated increase of the expression of CD40 but not of E-selectin in the endothelial cells and monocytes. In the scope of these analyses it could be shown that the IRF-1-protein expression is considerably weaker in the case of the mono-stimulation of the cells with IFNγ and in particular with TNFα than in the presence of both cytokines. According to this the transcription factors NF-κB and STAT-1 act synergistically in the case of the transcription of the IRF-1 gene, too (Ohmori et al., J. Biol. Chem., (1997), 272, 14899).

STAT-1 (GenBank Accession Number NM007315 and XM010893 and http://transfac.gbf de/cgi-bin/qt/getEntry.p1?t0149 respectively) belongs to a group of transcription factors which comprises at least 6 members. The product of the STAT-1 gene is expressed constitutively by most of the cells but usually exists as an inactive monomeric protein (91 kDa) in the cytoplasm. The tyrosine-phosphorylation of this p91-subunit and the subsequent association (dimerisation) of two of such p91-subunits (called STAT-1α) enables the transport of the from now on active transcription factor into the nucleus of the cell. A hetero-dimerisation with the p84-subunit of STAT-1β (differentially spliced product of the same gene) is also possible. The phosphorylation of the constitutively existing subunits occurs via cytoplasmic janus-kinases in dependency of the stimulus. So both janus-kinases (Jak1 and Jak2) are stimulated by IFNα (recruited better to the interferon receptor); on the contrary, the most important stimulus in terms of (patho)physiology for the activation of STAT-1, IFNγ, only stimulates Jak2. Different growth factors and peptide hormones (e.g. angiotensin II) activate STAT-1 as well; besides the intrinsic (growth factor) receptor-tyrosine-kinases also a mitogen-activated protein kinase (MAP-kinase) plays a role at this. In contrast to STAT-1α STAT-1β has no transactivating, i.e. the gene expression stimulating, activity. STAT-1 takes part in the expression of a series of potentially pro-inflammatory gene products in leukocytes, endothelial cells and smooth muscle cells whereby the activation of the transcription factor usually occurs in an IFNγ-dependent way. An exception is in particular the STAT-1-dependent expression of interleukin-6 in angiotensin II-stimulated smooth vascular muscle cells (Schieffer et al., Circ. Res. (2000), 87, 1195). Proteins, including also STAT-1, can be inhibited in their activity in very different ways. So e.g. anti-STAT-1-antibodies as well as natural or synthetic substances can be used which reduce the STAT-1-interaction with the DNA, i.e. reducing the transactivation activity. Further the signalling pathways (Jak1, Jak2, receptor tyrosine-kinases, MAP-kinases), which lead to the activation of STAT-1, could be inhibited. Preferred methods for the specific inhibition of the activity of STAT-1 are:

1. The neutralisation (squelching) of the activated transcription factor by a decoy-oligonucleotide,
2. the inhibition of the STAT-1-protein expression by means of an antisense-oligonucleotide and
3. the inhibition of the STAT-1-protein expression by means of an antisense-expression vector.

The herein used terms "decoy-oligonucleotide" or "cis-element decoy" refer to a double stranded DNA-molecule and a double stranded DNA-oligonucleotide respectively. Both DNA-strands exhibit a complementary sequence. In the present invention the cis-element decoy exhibits a sequence which is in accordance or similar to the natural STAT-1 core binding-sequence in the genome and which is bound by the transcription factor STAT-1 inside the cell. Thus the cis-element decoy acts as a molecule for the competitive inhibition (better neutralisation) of STAT-1.

One aspect of the present invention relates to the provision of a double stranded DNA-oligonucleotide which is able to bind the transcription factor STAT-1 in a sequence-specific way and has one of the following sequences whereas here only one strand each of the double stranded DNA-oligonucleotide is depicted and the complementary strand is also comprised:

| | |
|---|---|
| 5'-NTTNCBGDAAN-3', | (SEQ ID NO: 1) |
| 5'-ATTACCGGAAG-3', | (SEQ ID NO: 3) |
| 5'-ATTCCGGTAAG-3', | (SEQ ID NO: 5) |
| 5'-ATTCCTGGAAG-3', | (SEQ ID NO: 7) |
| 5'-ATTCCTGTAAG-3', | (SEQ ID NO: 9) |
| 5'-GTTCCAGGAAC-3', | (SEQ ID NO: 11) |
| 5'-GTTCCCGGAAG-3', | (SEQ ID NO: 13) |
| 5'-GTTCCGGGAAC-3', | (SEQ ID NO: 15) |
| 5'-TGTGAATTACCGGAAGTGAGA-3', | (SEQ ID NO: 17) |
| 5'-TGTGAATTACCGGAAGTG-3', | (SEQ ID NO: 19) |
| 5'-AGTCAGTTCCAGGAACTGACT-3', | (SEQ ID NO: 21) |
| 5'-ATGTGAGTTCCCGGAAGTGAACT-3', | (SEQ ID NO: 23) |
| 5'-ACAGTTCCGGGAACTGTC-3', | (SEQ ID NO: 25) |
| 5'-GACAGTTCCGGGAACTGTC-3', | (SEQ ID NO: 27) |
| 5'-GTGTATTCCGGTAAGTGA-3', | (SEQ ID NO: 29) |
| 5'-TTATGTGAATTCCTGGAAGTG-3', | (SEQ ID NO: 31) |

-continued

```
5'-CATGTTATGCATATTCCTGTAAGTG-3',  (SEQ ID NO: 33)
5'-TGTGAATTCCTGTAAGTGAGA-3',      (SEQ ID NO: 35)
5'-TGCATATTCCTGTAAGTG-3',         (SEQ ID NO: 37)
5'-ATATTCCTGTAAGTG-3'.            (SEQ ID NO: 39)
```

If a decoy-oligonucleotide according to the invention against STAT-1 but not a respective control-oligonucleotide in human endothelial cells is used, the cytokine-induced expression of CD40 (both in the mono-stimulation with IFNγ and in the combination of IFNγ and TNFα) is considerably inhibited by more than 50%. This holds true also for the expression of E-selectin and MCP-1 and interleukin-12 (p40), respectively, if the stimulation of the cells takes place with IFNγ and TNFα: and CD154, respectively. According to this an elimination of the STAT-1-activity brings about a highly significant inhibition of the expression of a group of pro-inflammatory gene products in human endothelial cells. Insofar one is to figure on a significant reduction of the endothelium-leukocyte-interaction (E-selectin, MCP-1), but also of the interaction of antigen-presenting cells (e.g. macrophages and B-lymphocytes) with T-lymphocytes (CD40, interleukin-12) in the scope of inflammatory diseases in the case of this therapeutic approach. Analogously this also holds true for the shown reduction of the cytokine-induced IRF-1-expression in the THP-1-monocytes (and thereby of the downstream expression of IRF-1-dependent genes) as well as of the cytokine-induced expression of the mentioned gene products including the inducible NO-synthase in the human smooth muscle cells.

A preferred method for the specific inhibition of the STAT-1-activity is therefore the use of double stranded DNA-oligonucleotides according to the invention, also called cis-element decoy or decoy-oligonucleotide, containing a binding site for STAT-1. The exogenous supply of a great number of transcription factor binding sites to a cell, in particular in a much higher number then present in the genome, generates a situation in which the majority of a certain transcription factor binds specifically to the respective cis-element decoy and not to its endogenous target binding sites. This approach for the inhibition of the binding of transcription factors to their endogenous binding site is also designated squelching. Squelching (or also neutralisation) of transcription factors using cis-element decoys was applied successfully to inhibit the growth of cells. Hereby DNA-fragments were used which contained the specific transcription factor binding site of the transcription factor E2F (Morishita et al., PNAS (1995) 92, 5855).

The sequence of a nucleic acid which is used for the prevention of the binding of the transcription factor STAT-1 is e.g. the sequence which STAT-1 naturally binds to inside the cell. STAT-1 binds specifically to the motive with the sequence 5'-NNNSANTTCCGGGAANTGNSN-3' in which the denotation is as follows: N=A, T, C or G and S=C or G. The exact consensus with the underlined bases and the distance between these bases are imperative for an effective binding of STAT-1. Therefore the cis-element decoy according to the invention may exhibit the following 11-mer consensus-core binding sequence: 5'-NTTNCBGDAAN-3' (SEQ ID NO: 1) in which the denotation is as follows: B=C, G or T, D=A, G or T and N=A, T, C or G. Furthermore the cis-element decoy can be larger than the 11-mer core binding sequence and be elongated at the 5'-end and/or at the 3'-end. According mutations in the region of the core binding sequence lead to the deprivation of the binding of STAT-1 to the decoy-oligonucleotide.

Since the cis-element decoy is a double stranded nucleic acid the DNA-oligonucleotide according to the invention comprises not only the sense- or forward-sequence but also the complementary antisense- or reverse-sequence. Preferred DNA-oligonucleotides according to the invention exhibit an 11-mer core binding sequence for STAT-1 as it is encompassed in SEQ ID NO: 3 to SEQ ID NO: 16.

But the cis-element decoy can also exhibit a sequence differing from the previous sequence and be longer than an 11-mer. Particularly preferred are the sequences such as encompassed in SEQ ID NO: 17 to SEQ ID NO: 40. These cis-element decoys contain 2 binding sites each for STAT-1.

The remark "2 binding sites" thereby relates to the sense- and antisense-strand. This listing of the preferred sequences is not limiting. It is obvious for a person skilled in the art that a multiplicity of sequences can be used as inhibitors for STAT-1 as long as they exhibit the previously denoted conditions of the 11-mer consensus core binding sequence and an affinity to STAT-1.

The affinity of the binding of a nucleic acid sequence to STAT-1 can be assessed by the use of the electrophoretic mobility shift assay (EMSA) (Sambrook et al. (1989), Molecular Cloning. Cold Spring Harbor Laboratory Press; Krezesz et al. (1999), FEBS Lett. 453, 191). This test system is suited for the quality control of nucleic acids which are intended for the use in the method of the present invention, or for the determination of the optimal length of a binding site. It is also suited for the identification of other sequences which are bound by STAT-1. For an EMSA, intended for the isolation of new binding sites, purified or recombinantly expressed versions of STAT-1 are most suitable which are applied in several alternating rounds of PCR-amplifications and a selection by EMSA (Thiesen and Bach (1990), Nucleic Acids Res. 18, 3203).

Genes known for encompassing STAT-1 binding sites in their promoter or enhancer regions or in the case of genes where there is already functional evidence for the importance of STAT-1 in their expression and which are therefore presumable targets for the specific squelching by the method of the present invention, are besides the CD40-, E-selectin-, inducible NO-synthase-, the interleukin-12 (p40)- and the MCP-1-gene further pro-inflammatory genes, e.g. IFNγ itself, the cytokine interleukin-6, the adhesion molecules ICAM-1, PECAM-1 (platelet endothelial cell adhesion molecule-1), RANTES (regulated upon activation, normal T-cell expressed, presumed secreted; solubly secreted by T-lymphocytes) and VCAM-1, the chemokines interleukin-8, IP-10 (interferon-inducible protein-10) and Mig (monokine induced by gamma-interferon) as well as the MHC-proteins I and II. Thereby it does not matter whether the expression of these genes is regulated by STAT-1 directly or indirectly (e.g. via the STAT-1-dependent expression of IRF-1).

The method of the present invention modulates the transcription of a gene or of genes in such a way that the gene or the genes, e.g. E-selectin, is/are not or less expressed. A reduced or suppressed expression in the scope of the present invention means that the rate of transcription is decreased in comparison to cells which are not treated with a double stranded DNA-oligonucleotide according to the present invention. Such a decrease can be determined e.g. by northern-blot-analysis (Sambrook et al., 1989) or RT-PCR (Sambrook et al., 1989). Usually such a decrease is at least a 2-fold, in particular at least a 5-fold, particularly at least a 10-fold decrease. The loss of activation can be achieved e.g.

if STAT-1 acts on a certain gene as a transcriptional activator and therefore the squelching of the activator leads to the loss of the expression of the target gene.

Furthermore the method of the present invention facilitates the release of inhibition of the expression of a gene as far as the expression is blocked by a constitutively active or (after a respective stimulation of the cell) by an activated transcription factor. An example for this is the release of inhibition of the expression of the prepro-endothelin-1-gene in native endothelial cells of the *V. jugularis* of the rabbit by a cis-element decoy against the transcription factor CCAAT/enhancer binding protein (Lauth et al., J. Mol. Med. (2000), 78, 441). By this means the inhibition of the expression of genes can be released whose products exert a protective effect e.g. against inflammatory diseases. So, e.g. the endothelial isoform of the NO-synthase, whose product NO plays a crucial role within the suppression of the expression of pro-inflammatory adhesion molecules and chemokines in endothelial cells, is down regulated by IFNγ (Rosenkranz-Weiss et al. (1994), J. Clin. Invest. 93, 1875). A cis-element decoy against STAT-1 can reverse this undesired effect by inhibiting the binding of STAT-1 to the according binding site in the promoter of the endothelial NO-synthase gene.

Oligonucleotides are usually rapidly degraded by endo- and exonucleases, especially by DNases and RNases in the cell. Therefore the DNA-oligonucleotides may be modified to stabilise them against the degradation so that a high concentration of the oligonucleotides is maintained in the cell during a longer period of time. Usually such a stabilisation can be obtained by the introduction of one or more modified internucleotide bonds.

A successfully stabilised DNA-oligonucleotide does not necessarily contain a modification at each internucleotide bond. Preferably the internucleotide bonds at the respective ends of both oligonucleotides of the cis-element decoy are modified. Thereby the last six, five, four, three, two or the last or one or more internucleotide bonds within the last six internucleotide bonds can be modified. Further different modifications of the internucleotide bonds can be inserted into the nucleic acid and the thereby emerging double stranded DNA-oligonucleotides can be assayed for the sequence specific binding to STAT-1 using the routine EMSA-test system. This test system allows the determination of the binding constant of the cis-element decoy and therefore the determination whether the affinity was changed by the modification. Modified cis-element decoys which still show a sufficient binding can be selected whereby a sufficient binding means at least about 50% or at least about 75%, and particularly preferred about 100% of the binding of the unmodified nucleic acid.

Cis-element decoys with modified internucleotide bonds which still show a sufficient binding can be tested if they are more stable in the cell than the unmodified cis-element decoys. The cells "transfected" with the cis-element decoys according to the invention are assayed for the amount of the still available cis-element decoys at different time points. Thereby preferably a cis-element decoy labelled with a fluorescent dye-stuff (e.g. Texas-red) or a cis-element decoy labelled radioactively (e.g. $^{32}P$) is used with a subsequent digital fluorescence microscopy and autoradiography or scintigraphy respectively. A successfully modified cis-element decoy has a half-life in the cell which is higher than the half-life of an unmodified cis-element decoy, preferably of at least about 48 hours, more preferred of at least about 4 days, most preferred of at least about 7 days.

Suitable modified internucleotide bonds are summarised in Uhlmann and Peyman ((1990) Chem. Rev. 90, 544). Modified internucleotide-phosphate-residues and/or non phosphorus-bridges in a nucleic acid which may be used in a method according to the present invention contain e.g. methylphosphonate, phosphorothioate, phosphorodithioate, phosphoramidate, phosphate-ester, whereas non-phosphorus internucleotide-analogues contain e.g. siloxane-bridges, carbonate-bridges, carboxymethylester-bridges, acetamidate-bridges and/or thioether-bridges. In the case of the use of phosphorothioate-modified internucleotide bonds they preferably should not lie between the bases cytosine and guanine since that may lead to an activation of the target cells of the cis-element decoy.

A further embodiment of the invention is the stabilisation of nucleic acids by the insertion of structural characteristics into the nucleic acids which increase the half-life of the nucleic acid. Such structures containing hairpin- and bell-shaped DNA, are disclosed in U.S. Pat. No. 5,683,985. At the same time, modified internucleotide-phosphate-residues and/or non-phosphorus-bridges can be introduced together with the mentioned structures. The thereby resulting nucleic acids can be assayed in the above described test system for binding and stability.

The core binding sequence may not only be present in a cis-element decoy but also in a vector. In a preferred embodiment the vector is a plasmid vector and in particular a plasmid vector which is able to replicate autosomally thereby increasing the stability of the introduced double stranded nucleic acid.

A cis-element decoy of the present invention is quickly taken up into the cell. A sufficient uptake is characterised by the modulation of the expression of one or more genes which are subject to a control by STAT-1. The cis-element decoy of the present invention preferably modulates the transcription of a gene or of genes after about 4 hours after contacting the cell, more preferred after about 2 hours, after about 1 hour, after about 30 minutes and most preferred after about 10 minutes. A typical mixture being used in such an experiment contains 10 µmol/l cis-element decoy.

Furthermore the present invention relates to the use of the cis-element decoys according to the invention in the manufacture of a medicament. Further the present invention relates to the use of the cis-element decoys according to the invention in the manufacture of a medicament for the prevention or therapy of cardio-vascular complications (e.g. restenosis after percutaneous angioplasty, stenosis of venous bypasses), the transplant rejection, the graft versus host disease (GVHD), the ischemia/refusion related damage in the context of surgical interventions, of immunological hypersensitivity reactions (type I to type V), auto-immune diseases (e.g. diabetes mellitus, multiple sclerosis, rheumatoid arthritis) as well as all other forms of acute, sub-acute and chronic inflammatory diseases, in particular of the joints (e.g. arthritis), of the respiratory organs (e.g. bronchial asthma, chronic bronchitis), of the skin (e.g. psoriasis, neurodermitis) and of the gastro-intestinal tract (e.g. ulcerative colitis, Chron's disease), including the septic shock.

Furthermore the present invention relates to a method for the modulation of the transcription of at least one gene in cells, particularly in endothelial cells, epithelial cells, leukocytes, smooth muscle cells, keratinocytes or fibroblasts, comprising the step of contacting the mentioned cells with a mixture containing one or more double stranded nucleic acids according to the invention which are able to bind sequence-specifically to the transcription factor STAT-1. A preferred method is e.g. the ex vivo treatment of a donation of bone marrow containing T-lymphocytes prior to the introduction into the recipient's body.

Furthermore the cis-element decoys according to the invention can be administered to the patients in a composition or be used in the method according to the invention. The composition (in the following called mixture) containing the cis-element decoys according to the invention is brought into contact with the target cells (e.g. endothelial cells, epithelial cells, leukocytes, smooth muscle cells, keratinocytes or fibroblasts). The aim of this contacting is the transfer of the cis-element decoys, which bind STAT-1, into the target cell (i.e. the cell which expresses pro-inflammatory gene products in a STAT-1-dependent manner). Therefore modifications of nucleic acids and/or additives or auxiliary substances known to be improving the penetration of the membrane can be used in the scope of the present invention (Uhlmann and Peyman (1990), Chem. Rev. 90, 544).

In a preferred embodiment the mixture according to the invention contains only nucleic acid and buffer. A suitable concentration of the cis-element decoys resides in the range of at least 0.1 to 100 µM, preferably at 10 µM, thereby one or more suitable buffers being added. One example of such buffers is Ringer's-solution containing 145 mmol/l Na$^+$, 5 mmol/l K$^+$, 156 mmol/l Cl$^-$, 2 mmol/l Ca$^{2+}$, 1 mmol/l Mg$^{2+}$, 10 mmol/l HEPES, 10 mmol/l D-glucose, pH 7,4.

In a further embodiment of the invention the mixture additionally contains at least one additive and/or auxiliary substance. Additives and/or auxiliary substances like lipid, cationic lipid, polymers, liposomes, nanoparticles, nucleic acid-aptameres, peptides and proteins which are DNA-bound or synthetic peptide-DNA-molecules are intended in order to (i) increase e.g. the introduction of nucleic acids into the cell, in order to (ii) target the mixture only to a sub-group of cells, in order to (iii) inhibit the degradation of the nucleic acid in the cell, in order to (iv) facilitate the storage of the mixture of the nucleic acids prior to their use. Examples for peptides and proteins or synthetic peptide-DNA-molecules are e.g. antibodies, fragments of antibodies, ligands, adhesion molecules which may all of them be modified or unmodified.

Additives that stabilise the cis-element decoys inside the cell are e.g. nucleic acid-condensing substances like cationic polymers, poly-L-lysine or polyethyleneimine.

The mixture which is used in the method of the present invention is preferentially applied locally by injection, catheter, suppository, aerosols (nasal and oral spray respectively, inhalation), trocars, projectiles, pluronic gels, polymers with a sustained release of medicaments, or any other device facilitating the local access. The ex vivo use of the mixture, used in the method of the present invention, allows a local access, too.

But the inhibition of the STAT-1 activity can not only be inhibited on protein level in the previously described methods but can be accomplished already before or during the translation of the transcription factor protein. The inhibition can be performed by a so called antisense-oligonucleotide. Antisense-oligonucleotides can inhibit the synthesis of a target gene on three different levels, during the transcription (prevention of the hnRNA-synthesis), during the processing (splicing) of the hnRNA resulting in the mRNA and during the translation of the mRNA into protein at the ribosomes. The method for the inhibition of the expression of genes by means of antisense-oligonucleotides is state of the art and well-known to persons skilled in the art. A further aspect of the present invention is an antisense-oligonucleotide which specifically inhibits the STAT-1 expression and has preferably one of the following sequences:

```
5'-TACCACTGAGACATCCTGCCAC-3',  (SEQ ID NO: 41)
5'-AACATCATTGGCACGCAG-3',      (SEQ ID NO: 42)
5'-GTGAACCTGCTCCAG-3'.         (SEQ ID NO: 43)
```

The antisense-oligonucleotide can be a single stranded DNA-molecule, an RNA-molecule or a single stranded DNA/RNA-hybrid-molecule. The antisense-oligonucleotide can furthermore exhibit one or more modified intemucleotide bonds, e.g. as described previously for the cis-element decoy. In the case of an antisense-oligonucleotide which is stabilised by phosphothioate-modified internucleotide bonds it is to be considered in particular that between the bases cytosine and guanine no phosphorothioate-modified internucleotide bonds are inserted because this leads to an IFNγ-similar activation of—in particular—immune-competent cells (e.g. endothelial cells) and would therefore, at least partly, foil the desired therapeutic effect.

The antisense-oligonucleotide can not only be administered as a single stranded nucleic acid molecule but can also be present in a vector. In a preferred embodiment the vector is a plasmid vector and in particular a plasmid vector which is able to replicate autosomally thereby increasing the stability of the introduced single stranded nucleic acid.

A further aspect of the present invention is therefore an antisense-expression vector being expressed inside the target cells by them after transfection and specifically inhibiting the STAT-1 expression. Thereby any available eukaryotic expression vectors according to the state of the art may be concerned. Preferably the pCI-plasmid of the company Promega (Catalogue No. E1731, GenBank Accession Number U47119) is concerned, in which e.g. a 2350 bp comprising segment of the STAT-1 gene (−121 to +2229, GenBank Accession Number XM010893) has been cloned in the opposite direction (3'→5'). This segment of the STAT-1 gene is flanked by two EcoRI restriction sites and contains a XhoI restriction site. Its expression is subjected to the control of the CMV-promoter. The entire plasmid (termed pCI/Stat1 AS) comprises 6365 bp.

The antisense-oligonucleotide-based attenuation of the STAT-1 protein expression also inhibits the cytokine-induced CD40-expression in human endothelial cells to the same extend as the decoy-oligonucleotide.

Furthermore the present invention relates to the use of the antisense-oligonucleotides according to the invention for the preparation of a medicament. Furthermore the present invention relates to the use of the antisense-oligonucleotides according to the invention for the preparation of a medicament for the prevention and/or therapy of cardio-vascular complications (e.g. restenosis after percutaneous angioplasty, stenosis of venous bypasses), the transplant rejection, the graft versus host disease (GVHD), the ischemia/refusion-related damage in the context of surgical interventions, immunological hypersensitivity reactions (type I to V), autoimmune diseases (e.g. diabetes mellitus, multiple sclerosis, rheumatoid arthritis) as well as all other forms of acute, sub-acute and chronic inflammatory diseases, in particular of the joins (e.g. arthritis), of the respiratory organs (e.g. bronchial asthma, chronic bronchitis), of the skin (e.g. psoriasis, neurodermitis) and of the gastro-intestinal tract (e.g. ulcerative colitis, Crohn's disease), including the septic shock.

The antisense-oligonucleotide according to the invention can also be used in a composition and be administered to the patients. The composition can be made up of stabilising additives or auxiliary substances facilitating e.g. the introduction of the antisense-oligonucleotides into the cell, targeting the composition to only one subgroup of cells, preventing e.g. the degradation of the antisense-oligonucleotides inside the cell, or facilitating e.g. the storage of the antisense-oligonucleotide prior to use.

The following figures and examples serve only for illustration and do not limit the scope of the invention in any respect.

1. Cell Culture

Human endothelial cells were isolated from the veins of the umbilical cord by treatment with 1.6 U/ml dispase in HEPES-modified tyrode-solution for 30 min. at 37° C. and were cultivated on gelatine-coated 6-well-tissue culture dishes (2 mg/ml gelatine in 0.1 M HCl for 30 min. at room temperature) in 1.5 ml M199 medium (Gibco Life Technologies, Karlsruhe, Germany), containing 20% foetal calf serum, 50 U/ml penicillin, 50 µg/ml streptomycin, 10 U/ml nystatin, 5 mM HEPES and 5 mM TES, 1 µg/ml heparin and 40 µg/ml endothelial growth factor. They were identified by their typical paving stone morphology, positive immune staining for the von Willebrandt-factor (vWF) and by fluorimetric detection (FACS) of PECAM-1 (CD31) as well as negative immune staining for smooth-muscular α-actin (Krzesz et al. (1999), FEBS Lett. 453, 191). The human monocyte-cell line THP-1 (ATCC TIB 202) was cultivated in RPMI 1640 medium (Life Technologies) containing 10% foetal calf serum, 50 U/ml penicillin, 50 µg/ml streptomycin and 10 U/ml nystatin. The human smooth muscle cells were isolated from dissected thymus veins by means of the explant-technology (Krzesz et al. (1999), FEBS Lett. 453, 191) and cultivated on gelatine-coated 6-well-tissue culture dishes (see above) in 1.5 ml Dulbecco's modified eagle medium, containing 15% foetal calf serum, 50 U/ml penicillin, 50 µg/ml streptomycin and 10 U/ml nystatin. They were identified by positive immune staining for smooth muscular α-actin.

2. RT-PCR-Analysis

The endothelial total-RNA was isolated with the Qiagen RNeasy kit (Qiagen, Hilden, Germany) followed by a cDNA-synthesis with a maximum of 3 µg RNA and 200 U Superscript™ II reverse transcriptase (Life Technologies) in a total volume of 20 µl according to the manufacturers protocol. For the adjustment of the cDNA-loading 5 µl (about 75 ng cDNA) of the resulting cDNA-solution and the primer pair (Gibco) for the elongation factor 1 (EF-1)-PCR with 1 U Taq DNA polymerase (Gibco) were used in a total volume of 50 µl. EF-1 served as an internal standard for the PCR. The PCR-products were separated on 1.5% agarose-gels containing 0.1% ethidium bromide and the intensity of the bands was determined densitometrically with a CCD-camera system and the One-Dscan gel analysis-software of Scanalytics (Billerica, Mass., USA) in order to adjust the volume of the cDNA in the following PCR-analysis.

All PCR-reactions were performed separately for each primer pair in a Hybaid OmnE Thermocycler (AWG; Heidelberg, Germany). The individual PCR-conditions for the cDNA of human endothelial cells from the umbilical cord were as follows: CD40 (product size 381 bp, 25 cycles, annealing temperature 60° C., (forward primer) 5'-CA-GAGTTCACTGAAACGGAATGCC-3' (SEQ ID NO: 44), (reverse primer) 5'-TGCCTGCCTGTTGCACAACC-3' (SEQ ID NO: 45)); E-selectin (product size 304 bp, 33 cycles, annealing temperature 60° C., (forward primer) 5'-AGCAAGGCATGATGTTAACC-3' (SEQ ID NO: 46), (reverse primer) 5'-GCATTCCTCTCTTCCAGAGC-3' (SEQ ID NO: 47)); EF-1 (product size 220 bp, 22 cycles, annealing temperature 55° C., (forward primer) 5'-TCT-TAATCAGTGGTGGAAG-3' (SEQ ID NO: 48), (reverse primer) 5'-TTTGGTCAAGTTGTTTCC-3' (SEQ ID NO: 49)); IL-12p40 (product size 281 bp, 30 cycles, annealing temperature 62° C., (forward primer) 5'-GTACTCCACAT-TCCTACTTCTC-3' (SEQ ID NO: 50), (reverse primer) 5'-TTTGGGTCTATTCCGTTGTGTC-3' (SEQ ID NO: 51)); rp132 (product size 368 bp, 20 cycles, annealing temperature 60° C., (forward primer) 5'-GTTCATCCG-GCACCAGTCAG-3' (SEQ ID NO: 52), (reverse primer) 5'-ACGTGCACATGAGCTGCCTAC-3' (SEQ ID NO: 53); MCP-1 (product size 330 bp, 22 cycles, annealing temperature 63° C., (forward primer) 5'-GCGGATCCCCTCCAG-CATGAAAGTCTCT-3' (SEQ ID NO: 54), (reverse primer) 5'-ACGAATTCTTCTTGGGTTGTGGAGTGAG-3' (SEQ ID NO: 55).

3. Electrophoretic Mobility Shift Assay (EMSA)

The nuclear extracts and [$^{32}$P]-labelled double stranded consensus-oligonucleotides (Santa Cruz Biotechnologie, Heidelberg, Germany), non-denaturing polyacrylamide-gel electrophoresis, autoradiography and supershift-analysis were performed as described in Krzesz et al. (1999), FEBS Lett. 453, 191. Thereby a double stranded DNA-oligonucleotide was used having the following single stranded sequence (the core binding sequence is underlined): SIE, 5'-GTGCAT<u>TTCCCGTAA</u>ATCTTGTC-3' (SEQ ID NO: 56). For the analysis of the extrusion of endogenous STAT-1 in nuclear extracts of cytokine-stimulated THP-1-cells (pre-monocytous human cell line) by the various cis-element decoys, a ratio of 30:1 (STAT-1 cis-element decoy: [$^{32}$P]-labelled SEE oligonucleotide (11 fmol)) was chosen in the EMSA-binding approach.

4. Decoy-Oligonucleotide-Technique

Double stranded decoy-oligonucleotides were generated with the complementary single stranded phosphorothioate-linked oligonucleotides (Eurogentec, Köln, Germany) as described in Krzesz et al. (1999), FEBS Lett. 453, 191. The cultivated human endothelial cells were pre-incubated at a concentration of 10 µM of the respective decoy-oligonucleotide for 4 hours. These were the conditions which were already previously optimised, based on the EMSA and RT-PCR-analysis. After this, the decoy-oligonucleotide containing medium was usually replaced by fresh medium. The single stranded sequences of the oligonucleotide were as follows (the underlined letters indicate phosphorothioate-linked bases, each of them in 5'-3' direction):

```
GATA-2,
CACTTGATAACAGAAAGTGATAACTCT    (SEQ ID NO: 57)

NF-κB,
AGTTGAGGGGACTTTCCCAGGC;        (SEQ ID NO: 58)

STAT-1,
CATGTTATGCATATTCCTGTAAGTG;     (SEQ ID NO: 33)

STAT-1-19mut,
GACAGTGCAGTGAACTGTC;           (SEQ ID NO: 59)

STAT-1-25mut,
CATGTTATGCAGACCGTAGTAAGTG.     (SEQ ID NO: 60)
```

5. Antisense-Oligonucleotide (ODN)-Technique

For an antisense-approach 100 ml OPTI-MEM®I culture medium was spiked with 15 µl lipofectin (Gibco Life Technologie, Karlsruhe, Germany) and incubated at room temperature (RT) for 45 minutes (solution A). Subsequently the antisense-ODN (Eurogentec, Köln, Germany) was added to a final concentration of 0.5 µM in 100 µl OPTI-MEM®I culture medium (solution B). After pooling the solutions A and B a further incubation for 15 minutes (RT) followed. At the start of the experiments 0.8 ml of the conventional cell culture medium of the culture of the endothelial cells (without heparin and endothelial growth factor) were added to an Eppendorf-tube containing the lipofectin-antisense-ODN-complexes and the cell culture medium of the culture of endothelial cells was replaced by the antisense-lipofectin-medium. The antisense-lipofectin-medium was removed after 4 hours and replaced by a fresh cell culture medium (with heparin and endothelial growth factor). The sequence of the STAT-1-antisense-ODN was 5'-T*A*CCA*C*T*G*A*G*A*C*A*T*CC*T*GCC*A*C-3' (* phosphorothioate-modified base; SEQ ID NO: 41).

6. Western Blot-Analysis

The human endothelial cells from the umbilical cord and smooth muscle cells from the thymus vein were cracked by subsequent freezing in liquid nitrogen and thawing at 37° C. (thermoblock, Kleinfelden, Germany) for five times. Protein extracts were prepared as described in Hecker et al. (1994), Biochem J. 299, 247. 20-30 µg protein were separated by means of a 10% polyacrylamide gel electrophoresis under denaturing conditions in the presence of SDS following the standard protocol and transferred to a BioTrace™ polyvinylidene fluoride transfer membrane (Pall Corporation, Roβdorf, Germany). The following primary antibodies were used for the immunological protein detection: CD40 protein (polyclonal, 1:2000 dilution, Research Diagnostics Inc., Flanders N.J., USA), STAT-1 protein (monoclonal, 1:5000 dilution, BD Transduction Laboratories, Heidelberg, Germany), IRF-1 protein (polyclonal, 1:2000 dilution, Santa Cruz Biotechnology, Heidelberg, Germany), iNOS protein (polyclonal, 1:3000 dilution, BD Transduction Laboratories, Heidelberg, Germany). The protein bands were detected after the addition of a peroxidase-linked anti-rabbit-IgG and—in the case of the use of the monoclonal primary antibody—by a respective anti-mouse-IgG (1:3000, Sigma, Deisenhofen, Germany) respectively by means of the chemiluminescence method (SuperSignal Chemiluminescent Substrate; Pierce Chemical, Rockford, Ill., USA) and a subsequent autoradiography (Hyperfilm™MP, Amersham Pharmacia, Biotech, Buckinghamshire, England). The loading and the transfer of equal protein amounts was shown after "stripping" of the transfer membrane (5 minutes 0.2 N NaOH, followed by washing with $H_2O$ for 3×10 minutes) by the detection of equal protein bands of M-actin with a monoclonal primary antibody and a peroxidase-linked anti-mouse IgG (both from Sigma-Aldrich, 1:3000 dilution).

7. Statistical Analysis

If not indicated differently all data in the figures and text are denoted as a mean value ±SEM of n experiments. The statistical evaluation was performed with the students t-test for unpaired data with a p-value <0.05 which was considered as statistically significant.

8. Detection of the Effect of Decoy-Oligonucleotides by Experimentation on Animals

8.1 Mouse

For the detection of the efficiency of the decoy-oligonucleotide-based therapeutic approach developed in the present application an animal experiment related proof-of-concept-study in the mouse with 8-10 animals per group was performed for the indication of an antigen-induced arthritis (for the model see Henzgen et al., Exp. Toxicol. Pathol. (1996), 48, 255). A single application of 0.25 nmol of the STAT-1-decoy-oligonucleotide (SEQ ID NO: 33) directly into the joint (intra-articular injection) reduced high significantly the antigen-induced swelling of the joint (by 35%), the intensity of the inflammatory response (by 70%), the articular destruction (by 80%), the total arthritis-score (by 70%) and the concentration of pro-inflammatory cytokines in the serum (e.g. interleukin-6 by 80%) during a period of 3-14 days. In contrast, the respective control-oligonucleotide had no therapeutic effect.

Furthermore it was noteworthy in this study that the contact dermatitis (type-IV-reaction) which was elicited in the skin 14 days after the induction of the arthritis—thereby the antigen is once more injected subcutaneously into the animals—was also high significantly inhibited (by 35%) in the decoy-oligonucleotide treated mice.

8.2 Guinea Pig

After allergisation of the guinea pigs for two times (Hartley, male, 350 g body weight) during a period of 7 days (on day 1 in one ear, on day 2 in the other ear with 50 µl of a 10% DNCB-solution in 50% acetone/50% olive oil each; on day 7 a boost in the skin of the neck with 15 µl of a 2% DNCB-solution in 95% acetone/5% olive oil) the contact dermatitis is elicited by a re-application of 2,4-dinitrochorobenzol (DNCB; 10 µl of a 0.5% solution of DNCB in 95% acetone/5% olive oil) on day 13 on one and more areas being of about 1 cm in size respectively on the shaved backs of the animals and assessed macroscopically and histologically 24 hours later. The contact dermatitis induced in such a way is histologically (Giemsa-staining) characterised by a pronounced formation of oedema and spongiosis in the area of the epidermis, an increase of apoptotic cells as well as massive infiltration by leukocytes (FIG. 8). The intradermal application of a STAT-1-decoy-oligonucleotide (SEQ ID NO: 19) but not of a mutated control-oligonucleotide (5'-TGTGGACCGTAGGAAGTG-3', SEQ ID NO: 61) 1 hour before the final DNCB-exposition led to a clear reduction of the mentioned histological parameters, i.e. in total to a significant attenuation of the inflammatory response.

The invention claimed is:

1. A decoy-oligonucleotide comprising a nucleic acid strand exhibiting a sequence selected from SEQ ID NO: 17-20.

2. The decoy-oligonucleotide according to claim 1, wherein said decoy-oligonucleotide exhibits modified internucleotide bonds.

3. A medicament comprising a decoy-oligonucleotide comprising a nucleic acid strand exhibiting a sequence selected from SEQ ID NO: 17-20.

4. The medicament according to claim 3, wherein said decoy oligonucleotide exhibits modified internucleotide bonds.

* * * * *

UNITED STATES PATENT AND TRADEMARK OFFICE
CERTIFICATE OF CORRECTION

PATENT NO. : 7,320,964 B2 Page 1 of 1
APPLICATION NO. : 10/491644
DATED : January 22, 2008
INVENTOR(S) : Markus Hecker et al.

It is certified that error appears in the above-identified patent and that said Letters Patent is hereby corrected as shown below:

In Title Page, Item (54) Title, please delete "MODULATION OF EXPRESSION OF STAT-1 DEPENDENT GENES" and insert --MODULATION OF THE EXPRESSION OF STAT-1-DEPENDENT GENES-- therefor.

In column 42, claim 4, line 14, delete "intemucleotide" and insert --internucleotide-- therefor.

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,320,964 B2 Page 1 of 1
APPLICATION NO. : 10/491644
DATED : January 22, 2008
INVENTOR(S) : Markus Hecker et al.

It is certified that error appears in the above-identified patent and that said Letters Patent is hereby corrected as shown below:

In Title Page, Item (54) Title and Column 1, lines 1 and 2, please delete "MODULATION OF EXPRESSION OF STAT-1 DEPENDENT GENES" and insert --MODULATION OF THE EXPRESSION OF STAT-1-DEPENDENT GENES-- therefor.

In column 42, claim 4, line 14, delete "intemucleotide" and insert --internucleotide-- therefor.

This certificate supersedes the Certificate of Correction issued May 13, 2008.

Signed and Sealed this

Third Day of June, 2008

JON W. DUDAS
*Director of the United States Patent and Trademark Office*

SEQUENCE LISTING

<160> NUMBER OF SEQ ID NOS: 61

<210> SEQ ID NO 1
<211> LENGTH: 11
<212> TYPE: DNA
<213> ORGANISM: Artificial Sequence

```
<220> FEATURE:
<223> OTHER INFORMATION: Description of Artificial Sequence: Synthetic
      Primer
<220> FEATURE:
<221> NAME/KEY: misc_feature
<222> LOCATION: (1)..(11)
<223> OTHER INFORMATION: n = g,a,c or t/u

<400> SEQUENCE: 1
nttncbgdaa n                                                          11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: misc_feature
<222> LOCATION: (1)..(11)
<223> OTHER INFORMATION: n = g,a,c or t

<400> SEQUENCE: 2
ntthcvgnaa n                                                          11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
attaccggaa g                                                          11

<210> SEQ ID NO 4
<211> LENGTH: 11
<212> TYPE: DNA
<213> ORGANISM: Artificial Sequence
<220> FEATURE:
<223> OTHER INFORMATION: cis element decoy

<400> SEQUENCE: 4
cttccggtaa t                                                          11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
attccggtaa g                                                          11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cttaccggaa t                                                          11
```

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
attcctggaa g                                                            11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
cttccaggaa t                                                            11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
attcctgtaa g                                                            11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cttacaggaa t                                                            11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gttccaggaa c                                                            11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gttcctggaa c                                                            11

```
<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gttcccggaa g                                                            11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cttccgggaa c                                                            11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gttccgggaa c                                                            11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gttcccggaa c                                                            11

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
tgtgaattac cggaagtgag a                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
tctcacttcc ggtaattcac a                                                 21
```

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
tgtgaattac cggaagtg                                                   18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
cacttccggt aattcaca                                                   18

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
agtcagttcc aggaactgac t                                               21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
agtcagttcc tggaactgac t                                               21

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
atgtgagttc ccggaagtga act                                             23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
agttcacttc cgggaactca cat                                             23

<210> SEQ ID NO 25
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
acagttccgg gaactgtc                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gacagttccc ggaactga                                                    18

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
gacagttccg ggaactgtc                                                   19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
gacagttccc ggaactgtc                                                   19

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gtgtattccg gtaagtga                                                    18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tcacttaccg gaatacac                                                    18

<210> SEQ ID NO 31
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
ttatgtgaat tcctggaagt g                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
cacttccagg aattcacata a                                              21

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
catgttatgc atattcctgt aagtg                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cacttacagg aatatgcata acatg                                          25

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
tgtgaattcc tgtaagtgag a                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
tctcacttac aggaattcac a                                              21

<210> SEQ ID NO 37
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 37
tgcatattcc tgtaagtg                                                   18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cacttacagg aatatgca                                                   18

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
atattcctgt aagtg                                                      15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
cacttacagg aatat                                                      15

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
taccactgag acatcctgcc ac                                              22

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
aacatcattg gcacgcag                                                   18

<210> SEQ ID NO 43
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 43
gtgaacctgc tccag                                                       15

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
cagagttcac tgaaacggaa tgcc                                             24

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
tgcctgcctg ttgcacaacc                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
agcaaggcat gatgttaacc                                                  20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
gcattcctct cttccagagc                                                  20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
tcttaatcag tggtggaag                                                   19

<210> SEQ ID NO 49
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 49
tttggtcaag ttgtttcc                                                   18

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
gtactccaca ttcctacttc tc                                              22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
tttgggtcta ttccgttgtg tc                                              22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
gttcatccgg caccagtcag                                                 20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
acgtgcacat gagctgccta c                                               21

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
gcggatcccc tccagcatga aagtctct                                        28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued

Primer

<400> SEQUENCE: 55
acgaattctt cttgggttgt ggagtgag                                      28

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
gtgcatttcc cgtaaatctt gtc                                           23

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
cacttgataa cagaaagtga taactct                                       27

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
agttgagggg actttcccag gc                                            22

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
gacagtgcag tgaactgtc                                                19

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
catgttatgc agaccgtagt aagtg                                         25

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 61
tgtggaccgt aggaagtg                                              18
```